United States Patent [19]
Wolfinger

[11] 3,993,633
[45] Nov. 23, 1976

[54] 2(1(2H)-PHTHALAZINONE)SULFENAMIDES VULCANIZATION INHIBITORS

[75] Inventor: Mark Dennis Wolfinger, Akron, Ohio

[73] Assignee: Monsanto Company, St. Louis, Mo.

[22] Filed: Sept. 11, 1975

[21] Appl. No.: 612,366

[52] U.S. Cl. .................. 260/79.5 B; 260/250 P; 260/79.5 C; 260/79.5 P; 260/775; 260/791
[51] Int. Cl.² ................. C08K 5/44; C07D 237/32
[58] Field of Search ................. 260/79.5 B, 79.5 C, 260/79.5 P, 250 P, 775, 791

[56] References Cited
UNITED STATES PATENTS

| | | | |
|---|---|---|---|
| 3,224,999 | 12/1965 | Walker | 260/250 P |
| 3,379,700 | 4/1968 | D'Amico | 260/250 P |
| 3,546,185 | 12/1970 | Coran et al. | 260/79.5 |
| 3,725,361 | 4/1973 | Boustany | 260/79.5 |

Primary Examiner—V. P. Hoke

[57] ABSTRACT

A novel class of 2-(1(2H)-phthalazinone)sulfenamides is described which sulfenamides are useful as inhibitors of premature vulcanization of rubber.

21 Claims, No Drawings

2(1(2H)-PHTHALAZINONE)SULFENAMIDES VULCANIZATION INHIBITORS

This invention relates to sulfenamides and more particularly to sulfenamides of 1-(2H)-phthalazinone. The invention also relates vulcanizable rubber compositions inhibited from premature vulcanization and to methods of inhibiting premature vulcanization of vulcanizable rubber compositions with 1(2H)-phthalazinone sulfenamides.

BACKGROUND OF THE INVENTION

It is known that certain sulfenamides having the characteristic nucleus

inhibit premature vulcanization of rubber. For example, see U.S. Pat. Nos. 3,546,185; 3,686,169; 3,705,135; 3,725,361; 3,732,271; 3,775,428; 3,780,001 and 3,862,051. The present invention concerns a different class of sulfenamides in which the aforesaid characteristic nucleus is part of a heterocyclic ring in which the dangling valence of nitrogen is satisfied by another nitrogen atom.

SUMMARY OF THE INVENTION

A class of 2-(1(2H)-phthalazinone)sulfenamides has been discovered which compounds are characterized by the formula

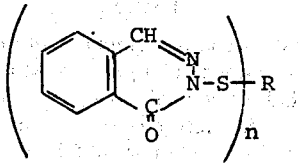

in which R is an organic radical and $n$ is an integer having a value equal to the valence of R. Preferredly, R is an aliphatic or aromatic radical and more preferredly is hydrocarbon, i.e., a radical which consists of only carbon and hydrogen.

An important subclass comprises compounds in which $n$ is one and R is alkyl of 1–20 carbon atoms, halo-lower alkyl, cycloalkyl of 5–12 carbon atoms, aralkyl of 7–12 carbon atoms, phenyl, naphthyl or substituted phenyl in which the substituents are lower alkyl, halo, preferredly chloro, nitro and sulfonyl. Compounds in which R is alkyl of 1–10 carbon atoms, cycloalkyl of 5–8 carbon atoms, aralkyl of 7–8 carbon atoms and phenyl are more preferred. Lower alkyl as used herein and in the claims refer to alkyl radicals of 1–5 carbon atoms. Examples of suitable alkyl radicals are methyl, ethyl, propyl, isopropyl, n-butyl, sec-butyl, isobutyl, tert-butyl, amyl, hexyl, 1-methylhexyl, heptyl, otyl, tert-octyl, decyl, dodecyl and eicosyl. Examples of suitable halo-lower alkyl radicals are trichloromethyl, trifluoromethyl, fluoromethyl, 2,2-dichloroethyl, 2,2-difluoroethyl, 1,2,2-trichloroethyl, 1,2,3-trifluoropropyl, 1-chlorobutyl and 2,2,2-trifluoromethyl. Examples of suitable cycloalkyl radicals are cyclopentyl, cyclohexyl, 2-methylcyclohexyl, 4-methylcyclohexyl, cycloheptyl, cyclooctyl, cyclodecyl and cyclododecyl. Examples of suitable aralkyl radicals are benzyl, α-methylbenzyl(1-phenethyl), α,α-dimethylbenzyl, α-ethylbenzyl, 2-phenethyl, 3-phenylpropyl, 4-phenylbutyl, xylyl, mesityl and 1-tolylethyl. Examples of suitable substituted phenyl radicals are o, m or p-tolyl, p-chlorophenyl, 2,4-dichlorophenyl, pentachlorophenyl, p-nitrophenyl, p-sulfonylphenyl, p-fluorophenyl, 2,4-dinitrophenyl, 2,4,6-trichlorophenyl and cumenyl.

Another important subclass comprises compounds in which $n$ is two and R is phenylene, methyl-phenylene, napthalene, cycloalkylene of 5–8 carbon atoms, straight or branched chain alkylene of 2–20 carbon atoms and interrupted alkylene of 2–20 carbon atoms in which alkylene is interrupted by oxygen, sulfur or phenylene. Compounds in which R is p-phenylene, cyclohexylene, alkylene of 2–10 carbon atoms and p-xylene are more preferred.

The compounds of this invention may be prepared by conventional procedures for preparing sulfenamides from amides and imides. One procedure comprises reacting sulfenyl chloride with 1(2H)-phthalazinone in the presence of a hydrogen chloride acceptor. Another procedure comprises reacting 2-halo-1(2H)-phthalazinone with the appropriate thiol.

Illustrative compounds of the invention are:
2-(methylthio)-1(2H)-phthalazinone
2-(ethylthio)-1(2H)-phthalazinone
2-(propylthio)-1(2H)-phthalazinone
2-(isopropylthio)-1(2H)-phthalazinone
2-(n-butylthio)-1(2H)-phthalazinone
2-(tert-butylthio)-1(2H)-phthalazinone
2-(trichloromethylthio)-1(2H)-phthalazinone
2-(trifluoromethylthio)-1(2H)-phthalazinone
2-(cyclopentylthio)-1(2H)-phthalazinone
2-(cyclohexylthio)-1(2H)-phthalazinone
2-(cyclooctylthio)-1(2H)-phthalazinone
2-(2-methylcyclohexylthio)-1(2H)-phthalazinone
2-(benzylthio)-1(2H)-phthalazinone
2-(α-methylbenzylthio)-1(2H)-phthalazinone
2-(α,α-dimethylbenzylthio)-1(2H)-phthalazinone
2-(phenylthio)-1(2H)-phthalazinone
2-(naphthylthio)-1(2H)-phthalazinone
2-(p-tolylthio)-1(2H)-phthalazinone
2(p-chlorophenylthio)-1(2H)-phthalazinone
1,2-bis(1(2H)-phthalazinon-2-ylthio)ethane
1,3-bis(1(2H)-phthalazinon-2-ylthio)propane
2,2-bis(1(2H)-phthalazinon-2-ylthio)propane
1,4-bis(1(2H)-phthalazinon-2-ylthio)butane
1,6-bis(1(2H)-phthalazinon-2-ylthio)hexane
1,10-bis(1(2H)-phthalazinon-2-ylthio)decane
1,18-bis(1(2H)-phthalazinon-2-ylthio)octadecane
1,2-di(1(2H)-phthalazinon-2-ylthio)propane
2,2'-bis(1(2H)-phthalazinon-2-ylthio)oxydiethane
2,2'-bis(1(2H)-phthalazinon-2-ylthio)thiodiethane
4,4'-bis(1(2H)-phthalazinon-2-ylthio)oxydibutane
1,1-bis(1(2H)-phthalazinon-2-ylthio)cyclohexane
1,2-bis(1(2H)-phthalazinon-2-ylthio)cyclohexane
1,4-bis(1(2H)-phthalazinon-2-ylthio)cyclohexane
α,α'-bis(1(2H)-phthalazinon-2-ylthio)p-xylene
α,α'-dimethyl-α,α'-bis(1(2H)-phthalazinon-2-ylthio)p-xylene
1,4-bis(1(2H)-phthalazinon-2-ylthio)benzene
2,5-di(1(2H)-phthalazinon-2-ylthio)toluene
and
1,5-bis(1(2H)-phthalazinon-2-ylthio)naphthalene.

Rubber stocks containing compounds of the invention exhibit reduced tendency to scorch. The method of inhibiting premature vulcanization according to the present invention comprises incorporating into vulcanizable elastomer a vulcanizing agent and in amount effective to inhibit premature vulcanization a 2-(1-(2H)-phthalazinone)sulfenamide as described above.

Rubber stocks containing delayed-action accelerators can be used in the process of this invention. Cheaper, more scorchy accelerators can also be used with an excellent degree of improvement. The improved vulcanizing process of this invention can be used advantageously to process stocks containing furnace blacks as well as stocks containing other types of blacks and fillers used in rubber compounding. The invention is also applicable to gum stocks.

The invention is applicable to rubber mixes containing sulfur-vulcanizing agents, peroxide-vulcanizing agents, organic accelerators for vulcanization and antidegradants. For the purposes of this invention, sulfur-vulcanizing agent means elemental sulfur or sulfur containing vulcanizing agent, for example, an amine disulfide or a polymeric polysulfide. The invention is applicable to vulcanization accelerators of various classes. For example, rubber mixes containing the aromatic thiazole accelerators which include benzothiazyl-2-monocyclohexylsulfenamide, 2-mercaptobenzothiazole, 2,2'-dithiobisbenzothiazole, N-tert-butyl-2-benzothiazole-sulfenamide, 2-benzothiazolyl, diethyldithiocarbamate, 2-(morpholinothio)benzothiazol and 2-(morpholinodithio)benzothiazol can be used. Amine salts of mercaptobenzothiazole accelerators, for example, the t-butyl amine salt of mercaptobenzothiazole, like salts of morpholine, and 2,6-dimethylmorpholine, can be used in the invention. Thiazole accelerators other than aromatic can be used. Stocks containing accelerators, for example, tetramethylthiuram disulfide, tetramethylthiuram monosulfide, aldehyde amine condensation products, thiocarbamyl sulfenamides, thioureas, metal dithiocarbamates, alkyldithiocarbamates, hexamethylenetetramine, xanthates, and guanidine derivatives, are substantially improved using the process of the invention. Examples of thiocarbamylsulfenamide accelerators are shown in U.S. Pat. Nos. 2,381,392, Smith assigned to Firestone, 2,388,236, Cooper assigned to Monsanto, 2,424,921, Smith assigned to Firestone, and British Pat. No. 880,912, Dadson assigned to Imperial Chemical Industries Limited. The invention is applicable to accelerator mixtures. The invention is applicable to stocks containing amine antidegradants. Rubber mixes containing antidegradants, for example, N-1,3-dimethylbutyl-N'-phenyl-p-phenylenediamine, N,N'-bis(1,4-dimethylpentyl-p)-phenylenediamine, and other phenylenediamines, ketone, ether, and hydroxy antidegradants and mixtures thereof, are substantially improved using the process of the invention. Mixtures of antidegradants, for example, a mixture of N-1,3-dimethylbutyl-N'-phenyl-p-phenylenediamine and N,N'-bis(1,4-dimethylpentyl)-p-phenylenediamine, furnish a much improved final product when used with the inhibitors of this invention.

The inhibitors of the invention can be used in natural and synthetic rubbers and mixtures thereof. Synthetic rubbers that can be improved by the process of this invention include cis-4-polybutadiene, butyl rubber, ethylene-propylene terpolymers, polymers of 1,3-butadiene, for example, 1,3-butadiene itself and of isoprene, copolymers of 1,3-butadiene with other monomers, for example, styrene, acrylonitrile, isobutylene, and methyl methacrylate. In general, stocks prepared with any sulfur-vulcanizable elastomer are improved which class includes chloroprene rubber and sulfur-vulcanizable urethane rubber. Diene rubbers are preferred and elemental sulfur is the preferred vulcanizing agent. Another sulfur vulcanizing agent is illustrated by 4,4'-dithiodimorpholine.

An alternative vulcanizing system applicable to sulfur vulcanizable rubber involves use of an organic peroxide vulcanizing agent. For example, dicumyl peroxide and other organic peroxides are listed in Materials and Compounding Ingredients for Rubber and Plastics compiled by the editors of Rubber World and printed by Publisher's Printing Co. 1975 under the section "Vulcanization and Curing Materials" pages 89–104. Such conventional organic peroxide vulcanizing agents are utilizable with the new inhibitors.

The quantity of inhibitor to be used in any particular application depends upon the components in the stock and the processing conditions to which the stock is subjected prior to vulcanization. The compounder can readily determine the optimum amount for his particular requirements by preparing stocks with various amounts of inhibitor and determining the scorch delay. The quantity usually is between 0.05 to 5.0 parts by weight inhibitor per 100 parts by weight elastomer. Concentrations from 0.10 to 3.0 parts per hundred are preferred. The higher quantities are used in the more scorchy stocks, for example, stocks containing scorchy blacks and amine antidegradants or in stocks which are subjected to high temperatures for times longer than normally encountered. Amounts within the range of 0.2 to 1.5 parts of inhibitor per 100 parts elastomer exert a powerful inhibiting effect.

DESCRIPTION OF PREFERRED EMBODIMENTS

Example 1

To a suitable reactor equipped with heating and stirring means, there is charged a solution of 2-sodium-1(2H)-phthalazinone (about 0.25 mole) in about 300 ml of xylene. A solution of cyclohexanesulfenyl chloride (about 0.25 mole) in about 50 ml of heptane is then added with stirring over a 30 minute period at 65° C. The mixture is stirred 30 additional minutes at 65° C, cooled to room temperature and held overnight. The mixture is filtered and the filtrate subjected to vacuum to strip off volatile components. The residue is taken up in 150 ml of heptane. A precipitate forms which is recovered by filtration. 2-(Cyclohexylthio)-1(2H)-phthalazinone, m.p. 85°–88° C recrystallized from ethanol, is obtained in 63% yield.

Example 2

To a suitable reactor equipped with heating and stirring means, there is charged a solution of 2-sodium-1(2H)-phthalazinone (about 0.107 mole) in about 300 ml of xylene. A solution of benzenesulfenyl chloride (about 0.11 mole) in 100 ml of benzene is added with stirring over a 30 minute period at 65° C. The mixture is stirred for one hour and cooled to room temperature. The mixture is filtered and the filtrate evaporated. The residue is slurried in 50 ml of heptane and filtered. 2-(Phenylthio)-1(2H)-phthalazinone, m.p. 117°–119° C recrystallized from aqueous ethanol, is obtained in 65% yield.

Example 3

To a suitable reactor equipped with heating and stirring means, there are charged 1(2H)-phthalazinone (0.10 mole) and triethylamine (0.11 mole) in about 200 ml of hexane. A solution of 2-propanesulfenyl chloride (about 0.11 mole) in 100 grams of hexane is added at room temperature over a 30 minute period and the mixture is stirred 30 additional minutes. The mixture is filtered and the solid is washed with water to remove amine salt by-product. 2-(Isopropylthio)-1(2H)-phthalazinone, m.p. 88°–90.5° C recrystallized from heptane is obtained. Identification is confirmed by nuclear magnetic resonance spectral analysis.

Example 4

To a suitable reactor, equipped with heating and stirring means, containing a solution of phthalazinone (0.10 mole) and triethylamine (0.12 mole) in about 200 ml of benzene, there is charged at room temperature perchloromethyl mercaptan (0.10 mole). The reaction mixture is stirred for one hour and is then left standing over the weekend. The amine salt byproduct is recovered by filtration and washed with benzene. The benzene is removed from the filtrate by evaporation. The residue is slurried in 200 ml of hexane and filtered. 2-(Trichloromethylthio)-1(2H)-phthalazinone, m.p. 127.5°–129.5° C recrystallized from heptane, is obtained.

Solutions of 2-sodium-1(2H)-phthalazinone of Examples 1 and 2 are prepared by distilling methanol from a mixture of phthalazinone, xylene and methanolic sodium methoxide.

The inhibitor activity of the compounds is illustrated by preparing sulfur-vulcanizable rubber stocks and comparing the properties of the stocks with and without the inhibitors present.

The cure characteristics of the stocks are determined at the indicated temperature by a Monsanto Oscillating Disk Rheometer. The time, $t_2$, required for a rise of two Rheometer units above the minimum reading and the time, $t_{90}$, required to obtain 90% of the Rheometer maximum torque is recorded. The difference of the two times, $t_{90}-t_2$, is a measure of the cure rate of the stocks.

The Rheometer maximum torque is the measure of the state of cure or the amount of cross-linking which has taken place during vulcanization. The time required to achieve optimum cure is determined from the Rheometer data and vulcanizates are prepared by heating stocks in a press for the indicated time. The scorch properties of the stocks are determined by a Mooney plastometer and the time ($t_5$) in minutes for the Mooney reading to rise five points above the minimum viscosity is recorded. Longer times on the Mooney scorch test indicate greater processing safety and inhibitor activity. The percent increase in scorch delay is calculated by dividing the Mooney scorch time of stock containing inhibitor by the Mooney scorch time of a control stock containing no inhibitor, subtracting 1.0 and multiplying by 100.

Rubber masterbatches are prepared comprising:

| Ingredients (Parts by weight) | Masterbatch A | Masterbatch B | Masterbatch C |
|---|---|---|---|
| Oil-extended styrene-butadiene rubber | 89 | — | — |
| Polybutadiene rubber | 35 | 50 | — |
| Natural rubber | — | 50 | 50 |
| Styrene-butadiene rubber blend | — | — | 60 |
| Carbon black | 67 | 56 | 70 |
| Zinc oxide | 3 | 3 | 3 |
| Stearic acid | 1 | 1 | 1 |
| Hydrocarbon processing oil | 15 | 10 | 10 |
| Hydrocarbon wax | 5 | 2.5 | — |
| Phenylenediamine antidegradant | 2 | 3 | — |
| Sulfur | 2 | 2.2 | 2.5 |
| Benzothiazole sulfenamide accelerator | 1.2 | 0.8 | 1 |
| Total Parts | 220.2 | 178.5 | 197.5 |

Stocks are prepared (all parts by weight) by incorporating the indicated amount of inhibitor with portions of the masterbatches. The stocks are then tested as previously described. The results are shown in Tables I, II and III.

TABLE I

| Stock | 1 | 2 | 3 | 4 | 5 | 6 |
|---|---|---|---|---|---|---|
| Masterbatch A | 220.2 | 220.2 | — | — | — | — |
| Masterbatch B | — | — | 178.5 | 178.5 | — | — |
| Masterbatch C | — | — | — | — | 197.5 | 197.5 |
| 2 (Cyclohexylthio)-1(2H)-phthalazinone | — | 0.25 | — | 0.25 | — | 0.25 |
| Mooney scorch time at 135° C | | | | | | |
| $t_5$, minutes | 17.0 | 22.0 | 10.2 | 15.6 | 17.3 | 25.0 |
| % increase in scorch delay | — | 29 | — | 53 | — | 44 |
| Rheometer data at 153° C | | | | | | |
| $t_2$, minutes | 9.4 | 11.4 | 6.2 | 8.7 | 10.5 | 12.0 |
| $t_{90}-t_2$ | 10.1 | 10.2 | 4.3 | 4.8 | 10.5 | 9.7 |
| Stress Strain data at 153° C | | | | | | |
| Cure time, minutes | 23 | 23 | 12 | 15 | 35 | 35 |
| 300% modulus, Kg/sq.cm. | 87.2 | 85.1 | 102.6 | 97.0 | 148.3 | 135.7 |
| Ult. ten. strength, Kg/sq. cm. | 191.2 | 193.3 | 196.7 | 191.2 | 201.8 | 189.1 |
| Ult. elongation, % | 530 | 570 | 530 | 500 | 430 | 400 |

TABLE II

| Stock | 1 | 2 | 3 | 4 | 5 | 6 | 7 |
|---|---|---|---|---|---|---|---|
| Masterbatch D* | 217.2 | 217.2 | 217.2 | 217.2 | 217.2 | 217.2 | 217.2 |
| 2(Phenylthio)-1(2H)-phthalazinone | — | 0.25 | 0.50 | — | — | — | — |
| 2(Trichloromethyltrio)-1(2H)-phthalazinone | — | — | — | 0.25 | 0.50 | — | — |
| 2(Isopropylthio)-1(2H)-phthalazinone | — | — | — | — | — | 0.25 | 0.50 |
| Mooney scorch time at 135° C | | | | | | | |
| $t_5$, minutes | 16.8 | 19.3 | 19.7 | 17.8 | 18.4 | 21.3 | 22.5 |
| % Increase in scorch delay | — | 15 | 17 | 6 | 10 | 27 | 34 |
| Rheometer data at 153° C | | | | | | | |

TABLE II-continued

| Stock | 1 | 2 | 3 | 4 | 5 | 6 | 7 |
|---|---|---|---|---|---|---|---|
| $t_2$, minutes | 4.1 | 7.0 | — | 6.1 | 6.3 | 7.3 | 5.1 |
| $t_{90}$-$t_2$ | 10.7 | 9.3 | — | 9.5 | 12.0 | 9.7 | 12.3 |
| Stress-Strain data at 153° C | | | | | | | |
| Cure time, minutes | 25 | 25 | 25 | 25 | 25 | 25 | 25 |
| 300% modulus, Kg/sq.cm. | 83.7 | 83.7 | 79.4 | 87.2 | 82.3 | 83.0 | 76.6 |
| Ult. tensile strength, Kg/sq.cm. | 167.3 | 168.7 | 170.1 | 156.8 | 158.9 | 158.2 | 166.6 |
| Ult. Elongation, % | 490 | 490 | 520 | 470 | 490 | 480 | 520 |

*Ingredients are the same as in Masterbatch A except Masterbatch D contains two parts by weight of hydrocarbon wax.

TABLE III

| Stock | 1 | 2 | 3 | 4 | 5 | 6 | 7 |
|---|---|---|---|---|---|---|---|
| Masterbatch E* | 172.5 | 172.5 | 172.5 | 172.5 | 172.5 | 172.5 | 172.5 |
| 2(Phenylthio)-1(2H)-phthalazinone | — | 0.25 | 0.5 | — | — | — | — |
| 2(Trichloromethylthio)-1(2H)-phthalazinone | — | — | — | 0.25 | 0.5 | — | — |
| 2(Isopropylthio)-1(2H)-phthalazinone | — | — | — | — | — | 0.25 | 0.5 |
| Mooney scorch time at 135° C | | | | | | | |
| $t_5$, minutes | 8.7 | 11.4 | 13.4 | 10.3 | 10.7 | 14.7 | 17.0 |
| % Increase in scorch delay | — | 31 | 54 | 18 | 23 | 69 | 94 |
| Stress-Strain data at 153° C | | | | | | | |
| Cure time, minutes | 12 | 13 | 13 | 13 | 15 | 13 | 15 |
| 300% modulus, Kg/sq.cm. | 68.2 | 77.3 | 76.6 | 77.3 | 75.2 | 67.5 | 70.3 |
| Ult. tensile strength, Kg/sq.cm. | 196.2 | 185.6 | 207.4 | 177.2 | 202.5 | 198.3 | 192.6 |
| Ult. Elongation, % | 540 | 510 | 560 | 550 | 550 | 560 | 550 |

*Ingredients are the same as in Masterbatch B except Masterbatch E contains 50 parts carbon black, 2 parts sulfur and one part accelerator.

The data demonstrate that the compounds of the invention are potent inhibitors of vulcanization. Significant improvement in scorch safety is achieved with amounts of 0.25 parts by weight inhibitor per 100 parts by weight rubber. The data indicate that alkylthio and cycloalkylthio compounds are especially potent inhibitors and that hydrocarbon alkylthio compounds are more active than compounds having electron withdrawing groups such as chlorine in the radical attached to sulfur. Comparison of the data of Tables II and III show that the inhibitors of the invention are more effective in vulcanizable compositions containing natural rubber. Other 2-(1(2H)-phthalazinone)sulfenamides of the invention inhibit premature vulcanization in a manner similar to the inhibitors illustrated.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A method of inhibiting premature vulcanization of sulfur-vulcanizable rubber containing a sulfur vulcanizing agent which comprises incorporating therein, in an amount effective to inhibit premature vulcanization, a compound of the formula

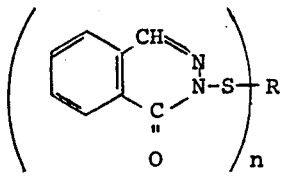

in which n is one or two; when n is one, R is alkyl of 1–20 carbon atoms, halo-lower alkyl, cycloalkyl of 5–12 carbon atoms, aralkyl of 7–12 carbon atoms, phenyl, naphthyl or substituted phenyl in which the substituents are lower alkyl, halo, nitro and sulfonyl; when n is two, R is phenylene, methyl-phenylene, napthalene, cycloalkylene of 5–8 carbon atoms, alkylene of 2–20 carbon atoms or said alkylene in which the alkylene chain is interrupted by oxygen, sulfur or phenylene.

2. The method of claim 1 in which the vulcanizing agent is elemental sulfur, the rubber is a diene rubber and contains an organic vulcanization accelerating agent.

3. The method of claim 2 in which n is one.

4. The method of claim 3 in which R is cycloalkyl of 5–8 carbon atoms.

5. The method of claim 4 in which R is cyclohexyl.

6. The method of claim 3 in which R is alkyl of 1–10 carbon atoms.

7. The method of claim 6 in which R is isopropyl.

8. The method of claim 3 in which R is phenyl.

9. The method of claim 3 in which R is 1-phenethyl.

10. The method of claim 2 in which n is two.

11. The method of claim 10 in which R is p-xylene.

12. A compound of the formula

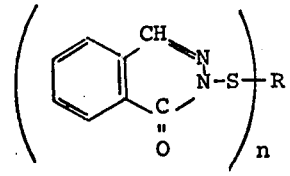

in which n is one or two; when n is one, R is alkyl of 1–20 carbon atoms, halo-lower alkyl, cycloalkyl of 5–12 carbon atoms, aralkyl of 7–12 carbon atoms, phenyl, naphthyl or substituted phenyl in which the substituents are lower alkyl, halo, nitro and sulfonyl; when n is two, R is phenylene, methyl-phenylene, napthaline, cycloalkylene of 5–8 carbon atoms, alkylene of 2–20 carbon atoms or said alkylene in which the alkylene chain is interrupted by oxygen, sulfur or phenylene.

13. The compound of claim 12 in which $n$ is one.
14. The compound of claim 13 in which R is cycloalkyl of 5–8 carbon atoms.
15. The compound of claim 14 in which R is cyclohexyl.
16. The compound of claim 13 in which R is alkyl of 1–10 carbon atoms.
17. The compound of claim 16 in which R is isopropyl.
18. The compound of claim 13 in which R is phenyl.
19. The compound of claim 13 in which R is 1-phenethyl.
20. The compound of claim 12 in which $n$ is two.
21. The compound of claim 20 in which R is p-xylene.

* * * * *